United States Patent [19]
Carroll, Jr. et al.

[11] Patent Number: 5,912,259
[45] Date of Patent: Jun. 15, 1999

[54] METHOD FOR TREATING AND PREVENTING NEURODEGENERATIVE DISORDERS BY ADMINISTERING A THIAZOLIDINONE

[75] Inventors: Richard Thomas Carroll, Jr., Toledo, Ohio; Richard Dennis Dyer, Ann Arbor, Mich.; Lillian Jane Robichaud, Ann Arbor, Mich.; Brenda DeRae Shivers, Ann Arbor, Mich.

[73] Assignee: Warner-Lambert Company, Morris Plains, N.Y.

[21] Appl. No.: 09/171,891

[22] PCT Filed: Jul. 1, 1997

[86] PCT No.: PCT/US97/11586

§ 371 Date: Oct. 28, 1998

§ 102(e) Date: Oct. 28, 1998

[87] PCT Pub. No.: WO98/02160

PCT Pub. Date: Jan. 22, 1998

Related U.S. Application Data

[60] Provisional application No. 60/021,571, Jul. 11, 1996.

[51] Int. Cl.$^6$ .................................................. A61K 31/41
[52] U.S. Cl. ............................................................... 514/369
[58] Field of Search ............................................... 514/369

[56] References Cited

FOREIGN PATENT DOCUMENTS 0 449 216 A1   10/1991   European Pat. Off. .
96/41626       12/1996   WIPO .

*Primary Examiner*—Theodore J. Criares
*Attorney, Agent, or Firm*—Charles W. Ashbrook

[57] ABSTRACT

Neurodegenerative disorders, i.e., Alzheimer's disease, stroke, multiple sclerosis and head trauma are treated with 5-[[{3,5-bis(1,1,-dimethylethyl)-4-hydroxyphenyl]methylene]-2-imino-4-thiazolidinone or a pharmaceutically acceptable salt thereof.

5 Claims, No Drawings

METHOD FOR TREATING AND PREVENTING NEURODEGENERATIVE DISORDERS BY ADMINISTERING A THIAZOLIDINONE

This application claims the benefit of U.S. Provisional Application No. 60/021,571 filed Jul. 11, 1996 and is a 371 of PCT/US97/11586 filed Jul. 1, 1997.

FIELD OF THE INVENTION

This invention concerns a method for treating and preventing neurodegenerative disorders such as stroke, head trauma, multiple sclerosis, and Alzheimer's disease, by administering a thiazolidinone.

BACKGROUND OF THE INVENTION

Neurodegenerative diseases are becoming more prevalent with the aging population. The most common neurodegenerative disorders include stroke and head trauma, and chronic disorders such as multiple sclerosis and Alzheimer's disease. Various causes have been postulated for many of these disorders, but no direct cause of neurodegeneration per se has been identified. For example, Alzheimer's disease, a condition afflicting millions of individuals, and becoming more common with the aging population, is a heterogeneous disease, clinically, genetically, pathologically, and biochemically. Diagnosis is based on the exclusion of other possible causes of dementia, and is more difficult in the early stages of the disease. Patients with Alzheimer's disease show a progressive loss of cognitive function beginning with seemingly benign memory lapses and culminating in severe dementia involving all domains of cognitive function. To date, only one therapeutic approach has been approved for the clinical treatment for Alzheimer's disease, that being acetylcholinesterase inhibitors. However, their clinical effectiveness is somewhat limited.

We have now discovered that neurodegenerative disorders such as Alzheimer's disease, stroke, head trauma, and multiple sclerosis can be treated with a thiazolidinone, specifically a compound known as 5-[[3,5-bis-(1,1-dimethylethyl)-4-hydroxyphenyl]methylene]-2-imino-4-thiazolidinone, or a pharmaceutically acceptable salt thereof. The compound is described in U.S. Pat. No. 5,143,928. It inhibits the activities of both cyclooxygenase and 5-lipoxygenase, and is useful as an anti-inflammatory agent. An object of this invention is to provide a method for treating and preventing neurodegenerative disorders utilizing the compound.

SUMMARY OF THE INVENTION

This invention provides a method for treating and preventing neurodegenerative disorders comprising administering to a patient in need of treatment an effective amount of 5-[[3,5-bis(1,1-dimethylethyl)-4-hydroxyphenyl]methylene]-2-imino-4-thiazolidinone or a pharmaceutically acceptable salt thereof. A preferred embodiment utilizes the methanesulfonate salt. Also preferred is the Z geometric isomer. Another preferred embodiment is prevention or treatment of Alzheimer's disease. In another embodiment, the neurodegenerative disorder prevented or treated is multiple sclerosis. In still another embodiment, the disorder treated is stroke or head trauma.

DETAILED DESCRIPTION OF THE INVENTION

The term "thiazolidinone" means the specific compound named above, its pharmaceutically acceptable salts, and its individual geometric isomers. The thiazolidinone to be employed in the method of this invention is prepared and formulated as described in U.S. Pat. No. 5,143,928 which is incorporated herein by reference. All that is required to practice the method of this invention is to administer an effective amount of the thiazolidinone to a subject suffering from a neurodegenerative disorder or at risk of developing such disorder and in need of treatment. The term "effective amount" means the dosage of the thiazolidinone needed to elicit a positive clinical response to the neurodegenerative disorder or to prevent the disorder without causing unacceptable adverse side effects. While the specific dosage will vary somewhat depending upon the severity of the disorder being treated, the individual patient, and the discretion of the attending medical practitioner, the dosage that generally is effective to treat and prevent neurodegenerative disorders will be from about 0.5 to about 500 mg of thiazolidinone per day of treatment. Commonly utilized dosage regimes are from about 1 to 50 mg, administered from one to about four times a day. A preferred route of administration is oral, although parenteral and transdermal administration are also contemplated. Controlled release formulations, particularly in the form of skin patches and the like, are particularly well suited for treating elderly patients.

The thiazolidinone to be utilized in the method of this invention is ideally suited for several reasons. First, it is relatively benign to the GI tract and kidneys, making long-term administration feasible. Second, it has a relatively long half-life, thereby enabling effective treatment with fewer dosings, which is of significant importance for elderly patients. Third, the thiazolidinone readily crosses the blood-brain barrier, thereby making it particularly well suited for treating and preventing disorders affecting brain function. The thiazolidinone has been evaluated in a number of biological systems which establish its effectiveness in treating and preventing neurodegenerative disorders. The following detailed examples illustrate some of the biological assays employed to establish the efficacy of the thiazolidinone. In all studies described below, the specific compound employed was (Z)-5-[[3,5-bis(1,1-dimethylethyl)-4-hydroxyphenyl]methylene]-2-imino-4-thiazolidinone methanesulfonate, also identified as CI-1004.

EXAMPLE 1

The following assay establishes that the thiazolidinone is effective in ameliorating the neurodegeneration in animals induced by intrastriatal injection of the neurotoxin N-methyl-D-aspartate (NMDA).

Intrastriatal injections of NMDA (15 nmol/0.5 µL) were performed in male and female Sprague-Dawley rat pups (Charles River Laboratory, Portage, Mich.) on Postnatal Day (PND) 7. The animals were anesthetized with ether, and the calvarium was exposed by a midline incision through the skin. The rat pups were placed in a plaster of paris mold that was secured to a small animal stereotaxic instrument (Kopf Instruments). NMDA (Sigma) was dissolved in 0.1 M phosphate-buffered saline (PBS) adjusted to pH 7.4 with 1 N NaOH. Injections of NMDA (15 mmol/0.5 µL) were placed in the middle of the right posterior corpus striatum (coordinates relative to Bregma; AP −2.0 mm, ML 2.5 mm, at a depth of 4.0 mm from the dura) with a 26-gauge Hamilton syringe. The syringe was left in place for 2 minutes following the injections to limit leakage. Temperature of the animals was kept constant after surgery in a thermostatically controlled environment (HovaBator chick incubator; BFG Corp., Savannah, Ga.) set at 35° C. to 36° C. for 1 hour after the last drug or vehicle injection. Drug solutions were prepared in PBS and injected intraperitoneally (0.05 mL volume) 15 minutes, and 2.25 hours after intrastriatal injection of NMDA. Control animals received equal volumes of PBS.

After surgery, all animals were returned to the mothers for 5 days, and decapitated on PND 12. The brains were removed, the cerebral hemispheres were separated, and wet weights of each hemisphere were determined individually. Differences of the hemispheric weights were compared for each animal using the formula: $100\times(C-I/C)=$percent damage, a value that indicates the severity of damage of the injected (I) cerebral hemisphere relative to that of the uninjected contralateral (C) hemisphere. Percent protection is used to indicate the relative protection of the neuroprotective compound compared to the control and was calculated as: $100\times[1-(\%\ damage_{treated}/\%\ damage_{control})]$. Data were expressed as mean percent damage$\pm$S.E.M. in all groups. Independent t-tests were used for statistical comparisons. Previous experiments demonstrated that hemispheric weights correlated closely with reductions in both choline acetyltransferase activity and regional cross-sectional areas inspected histologically ($\alpha^2=0.99$, $p<0.001$, linear regression). This same study also showed that intrastriatal PBS injections do not cause significant damage.

RESULTS

NMDA (15 nmol/0.5 $\mu$L) injected into the posterior striatum produced a $20.6\pm1.8\%$ (N=10) reduction in the wet weight of the cerebral hemisphere ipsilateral compared to control animals that were given an intraperitoneal injection of PBS. All control animals survived to PND 12. The thiazolidinone, at the doses of 2×10 and 2×30 mg/kg, significantly prevented NMDA-induced injury ($28.1\pm9.2\%$ and $49\pm8.2\%$, respectively; $p<0.04$ and $p<0.001$). One animal dosed with thiazolidinone (2×30 mg/kg) did not survive to PND 12. Protection at the 2×30 mg/kg dose was comparable to that provided by the 2×30 mg/kg of indomethacin.

Over-activation of excitatory amino acid neurotransmission, especially that mediated by the NMDA receptor, is responsible for much of the neuronal damage resulting from cerebral ischemia, such as that found following a stroke or neural trauma. The fact that the thiazolidinone ameliorates NMDA-induced injury thus establishes that it is useful in treating neuronal injury resulting from cerebral ischemia.

EXAMPLE 2

The thiazolidinone was evaluated in a mouse model of experimental autoimmune encephalomyelitis (EAE). The compound was administered orally to mice sensitized with a fragment of mouse myelin basic protein to induce EAE. Two experiments were conducted using the same protocol and neurological evaluations. Test animals were dosed for 21 days, beginning 4 hours before sensitization on Day 1. The effects of the thiazolidinone were compared to a control group of mice sensitized identically and dosed with vehicle alone. Neurological evaluations continued after cessation of drug treatment. The values reported in Tables 1 and 2 below include responses during drug treatment only.

Drug Preparation and Treatments

The thiazolidinone was homogenized manually with an aliquot of warm vehicle (0.5% hydroxypropyl methylcellulose with 0.2% Tween 80 in water) in glass mortar tubes and homogenizing pestle. The smooth drug paste was gradually suspended in vehicle. Mice were dosed with drug and/or vehicle, 10 mg/kg in groups of ten (Experiment 1) or twenty (Experiment 2). Mice were dosed from Experiment Day 1 to Day 21. A sham-sensitized group was similarly dosed with vehicle or thiazolidinone 30 mg/kg (Experiment 1).

Sensitization

Female mice, strain PL/J(F1)×SJL/J from Jackson Labs, were sensitized s.c. (0.05 cc×2) at the base of the tail with an emulsion containing equal parts of mouse myelin basic protein (MBP) fragment (amino acids 1–9 of the N-terminus of MBP) in saline and Difco Complete Freund's Adjuvant (CFA) fortified with heat killed desiccated *Mycobacteria tuberculosis* (MT). Each mouse received 300 $\mu$g of the MBP fragment (230 $\mu$g free base) and 200 $\mu$g MT followed by retrobulbar (i.v.) injection of 200 ng of *B. pertussis* toxin in 0.2 cc of saline. Forty-eight hours later, mice received a second injection of *B. pertussis* toxin. Mice in Experiment 1 were 8 to 9 weeks old; mice in Experiment 2 were 11 weeks old.

Neurological Assessment

Animals were weighed and evaluated for symptoms of EAE before sensitization and frequently for 21 days. EAE score: (0.5=slight limp tail, 1=limp tail or slow to right, 1.5=slight limp tail and slow to right, 2=paresis/mild paralysis or incontinence, 2.5=mild paralysis and slow to right or complete paralysis (one hind limb), 3=hind limb paralysis (both), 3.5=hind limb paralysis (both) and limp torso; 4=additional fore limb paralysis, 4.5=head movement only, 5=moribund, death after previous EAE symptoms). Evaluators were blinded as to drug treatments and previous behavioral scores.

Disease symptoms were compared among groups for EAE severity, incidence, time to onset, cumulative score, deaths, and weight loss. Peak EAE score: the mean of highest score of each mouse in a group, independent of duration of symptoms; EAE incidence: the mean number of mice showing symptoms of EAE, defined as having EAE scores on any three consecutive days that total$\geq 3.0$. EAE deaths: An animal that died must have presented previous evidence of an EAE score greater than 0.5; EAE onset: the first of a 3-day series scoring a total of $\geq 3.0$. A Cumulative EAE score is calculated for each animal. A mean of all animals' cumulative score is then determined for each day. Maximum weight loss: the mean of the lowest weight for each animal in a group. (Note: The Cumulative EAE score and the Maximum weight loss can be influenced by death which eliminates severely diseased animals. The number of days that animals are scored also affects the cumulative score and can only be compared "within-trial"). Mice that die from dosing trauma or with no previous symptoms of EAE are deleted from the study. Experimental groups were assumed to be similar and were compared for statistical significance by a two-tailed t-test ($p\leq 0.05$).

RESULTS

Experiment 1

The sensitized vehicle controls exhibited robust symptoms of EAE, as shown by the daily EAE score and a spectrum of neurological criteria (Table 1). The control group had 3/10 EAE deaths, while sham-sensitized mice treated with vehicle or thiazolidinone 30 mg/kg group showed little symptoms of disease and no deaths (Table 1). Sensitized mice treated with 3 or 10 mg/kg of thiazolidinone did not show significantly reduced EAE scores (versus vehicle controls) (Table 1) to Day 21, although the 10 mg/kg group showed a suggestion of inhibition of daily EAE scores, reduced incidence, cumulative EAE scores, and weight loss.

Sensitized mice treated with 30 mg/kg of thiazolidinone had three deaths at ≦Day 10. Their only previously exhibited 8symptoms were deficits in righting reflex (score=1.0). Data for that group were calculated in two ways: (A) deaths designated EAE (n=9) and (B) deaths designated non-EAE related, with those mice deleted from the study. Both methods of calculation showed a tendency to reduced daily EAE scores from Days 10 to 21, although a statistically significant reduction was seen only on Day 15 ($p \leq 0.05$). Calculated using Method A, there was no significant reduction in overall EAE symptoms (Table 1) although a suggestion of inhibition was seen similar to the 10 mg/kg group. Calculated using Method B, there was a significant reduction in the peak EAE score and weight loss (Table 1).

Experiment 2

The previous study was repeated with three larger groups of sensitized mice treated with (1) vehicle, (2) thiazolidinone at 10 mg/kg, or (3) thiazolidinone at 30 mg/kg. The onset of EAE in the sensitized vehicle controls was similar to Experiment 1, although the daily EAE scores from Days 13 to 19 were slightly higher with fewer remissions from Day 20 to 52, and more severe overall neurological criteria (Table 1 versus Table 2).

The thiazolidinone at 10 or 30 mg/kg had no effect on the daily EAE score or overall EAE responses (peak score, incidence, onset, deaths, cumulative score or weight loss) (Table 2). Deaths in all groups were preceded by symptoms of EAE.

The EAE model produces a syndrome similar to that seen in multiple sclerosis. The data generated on the thiazolidinone indicates it reduces some of the neurological symptoms in EAE and is thus useful for treating patients suffering from multiple sclerosis.

TABLE 2

Mouse Experimental Autoimmune Encephalomyelitis (EAE)

| Treatment/ Oral Dose Day 1: 03/11/96 | EAE | | | | | Weight |
|---|---|---|---|---|---|---|
| | Peak Score | Inci- dence | Onset (Day) | Deaths | Cumulative Score | Loss (max %) |
| Control | 4.3 ± 0.2 | 20/20 | 11.6 | 7/20 | 30.5 ± 2.5 | 80.8 ± 1.4 |
| CI-1004 10 mg/kg | 4.5 ± 0.7 | 19/19 | 11.8 | 10/20 | 31.3 ± 3.6 | 76.9 ± 1.4 |
| CI-1004 30 mg/kg | 4.3 ± 0.2 | 20/20 | 12.4 | 8/20 | 28.9 ± 2.7 | 81.8 ± 1.6 |

EXAMPLE 3

Additional testing of the thiazolidinone has established that it inhibits nitric oxide synthase activity in lipopolysaccharide-stimulated microglial cells and in mixed cortical cell cultures. The decrease of nitric oxide production is a result of inhibiting nitric oxide synthase induction and is further evidence that the thiazolidinone will limit damage to brain tissue.

BV-2 microglia were grown in 6-well tissue culture plates in DMEM/F12 media supplemented with 10% fetal calf serum. Prior to activation, cells were given fresh media containing various amounts of thiazolidinone. One hour after drug treatment, microglia were activated with lipopolysaccharide (LPS, 4 μg/mL) and placed in an incubator at 37° C. in an atmosphere containing 5% $CO_2$. After 16 hours, cultures were evaluated for inducible nitric oxide synthase (iNOS) activity and expression. iNOS activity was determined using the Griess reaction. Cell-free culture media was mixed with an equal volume of Griess reagent (one volume of 1.0% sulfanilamide in 5% phosphoric acid mixed with one volume of 0.1% naphthylenediamine dihydrochloride in water) and incubated for 5 minutes at room temperature. Absorbance was measured at 560 nm and the concentration within a sample was determined using sodium nitrite as standard. iNOS expression was evaluated by extracting cellular protein and performing Western blot analysis using a monoclonal antibody specific for iNOS.

TABLE 1

Mouse Experimental Autoimmune Encephalomyelitis (EAE)

| Treatment/ Oral Dose Day 1: 11/20/95 | EAE | | | | | |
|---|---|---|---|---|---|---|
| | Peak Score | Incidence | Onset (Day) | Deaths | Cumulative Score | Weight Loss (max %) |
| Sham | 0.8 ± 0.4 | 0/9 | — | 0/9 | 1.3 ± 0.5 | 95.8 ± 0.6 |
| Sham-CI-1004 30 mg | 0.8 ± 0 | 0/9 | — | 0/9 | 1.4 ± 0.6 | 98.5 ± 1.1 |
| Control | 3.9 ± 0.4 | 10/10 | 12.4 ± 0.6 | 3/10 | 17.9 ± 3.2 | 78.4 ± 2.9 |
| CI-1004 3 mg | 3.7 ± 0.3 | 10/10 | 12.2 ± 0.3 | 2/10 | 20.3 ± 1.7 | 80.1 ± 2.0 |
| CI-1004 10 mg | 3.0 ± 0.6 | 7/10 | 12.1 ± 1.5 | 2/10 | 10.9 ± 1.7 | 85.8 ± 3.0 |
| CI-1004 30 mg[a] | 3.1 ± 0.6 | 7/9 | 12.7 ± 2.2 | 3/9 | 10.9 ± 3.4 | 86.1 ± 3.8 |
| CI-1004 30 mg[b] | 2.1 ± 0.6 ($p < 0.05$) | 4/6 | 16.0 ± 2.1 | 0/6 | 9.4 ± 3.4 | 90.4 ± 4.6 ($p < 0.05$) |

[a]Deaths designated due to EAE.
[b]Deaths designated due to unknown causes; values removed from calculations.

Results demonstrate that the thiazolidinone inhibited the production of nitric oxide in activated BV-2 microglia with an $IC_{50}$ of 2.4 $\mu$M. Examination of iNOS enzyme by Western blot analysis showed that the observed decrease in activity correlated with a decrease in protein expression. Taken together, these data demonstrate that the thiazolidinone can prevent the expression of iNOS in activated microglia reducing the quantity of neurotoxic nitric oxide liberated by these cells.

Experiments using mixed cortical cultures were performed as described above. The cells were collected and cultured as described in EXAMPLE 4 and were grown in 6-well plates. In these experiments, the thiazolidinone (10 $\mu$M) also prevented the increase in nitric oxide synthase activity associated with LPS activation of the cultures. When non-LPS activated cultures were treated with the thiazolidinone, a significant decrease in basal NO production was also observed. This decrease in NO production is thought to be due to the inhibition of iNOS expression associated with normal glial activation in these cultures. This further indicates the usefulness of the thiazolidinone in reducing neurotoxicity associated with neuroinflammation.

EXAMPLE 4

The thiazolidinone also blocks production of the cytokine IL-1$\beta$, as well as cell-surface expression of ICAM-1 and E-selectin. The compound also protects against oxygen and glucose deprivation in vitro.

Cerebral ischemia can be modeled in vitro by lowering oxygen and glucose in the media of cortical neurons. For this study, cortical neurons were isolated from fetal Sprague-Dawley rat brains on Day E18. Cortical hemispheres were sectioned, dissociated, and triturated in Hank's Balanced Salt Solution (HBSS) containing 0.1% trypsin. Cell concentration was adjusted to 620,000 cells/mL by the addition of Dulbecoo's Modified Eagles Medium (DME) and Ham's Nutrient mixture F-12 (F12) 1:1 supplemented with heat-inactivated 10% horse serum and 6% fetal calf serum. A 100 $\mu$L aliquot of cell suspension was pipetted into each individual well of a 96-well polyethylenimine-coated culture plate. After 4 days in an incubator at 37° C. in an atmosphere of 8% $CO_2$, 100 $\mu$L medium was drawn off from each well and replaced with 100 $\mu$L of DME/F12 with 10% horse serum to which 30 $\mu$g/mL 5-fluoro-2-deoxyuridine and 70 $\mu$g/mL uridine were added to prevent further division of the glial cells. Cultures were read every 2 to 3 days thereafter by half volume (100 $\mu$L) replacement with DME/F12 (10% horse serum).

Cells were exposed to an hypoxic/hypoglycemic environment (91% $N_2$/8% $CO_2$/1% $O_2$, 1 mM glucose, 37° C.) for varying times in 50 $\mu$L HBSS. Cultures were then returned to the normoxic incubator (21% $O_2$/8% $CO_2$, 25 mM glucose) and quantitative assessment of cell death made 24 hours later by measurement of the intracellular enzyme lactate dehydrogenase (LDH). Cells were exposed for 1 hour to the thiazolidinone or other drugs prior to the induction of hypoxia/hypoglycemia. A concentration of 1 $\mu$M of the thiazolidinone had no effect, but 10 $\mu$M significantly increased the duration of hypoxia/hypoglycemia before the cells lost viability. For instance, 4 hours of exposure to hypoxia/hypoglycemia killed approximately 50% of the neurons in control conditions, but this exposure in cells treated with 10 $\mu$M of the thiazolidinone produced no neuronal death. Similar effects were seen with 100 $\mu$M indomethacin. These results are similar to those seen with NMDA antagonists in this model system. Since similar conditions occur in the brain following occlusion of a blood vessel or trauma, these results establish that the thiazolidinone is useful in the treatment of neurological disorders resulting from cerebral ischemia.

EXAMPLE 5

The thiazolidinone was shown to decrease neurodegeneration in canine leptomeningeal smooth muscle cells in the following test.

Canine smooth muscle cells were isolated from freshly obtained old dog meninges. Each dog had served previously as a vehicle control in toxicological studies and was sacrificed humanely with an overdose of barbiturate. Old dogs have an angiopathy resembling the human condition. Smooth muscle cells are the site of cerebral vessel myopathy occurring in the Dutch form of Alzheimer's disease. The compromise of these cells ultimately leads to a cerebrovascular accident and the death of some humans.

Cells from the meninges were dissociated and kept in culture in 10% fetal calf serum and Dulbecco's minimal essential media with antibiotics for about 1 week on tissue culture plates before use in biochemical studies or transferal to uncoated microscope slides for morphological studies. These smooth muscle cells represent brain blood vessel cells and they can be passaged several times. For inducing cytotoxicity, the cells were treated, in serum-free media, with 10 to 20 $\mu$M of amyloid $\beta$-peptide that was 42 amino acids long. This peptide corresponds to the human $\beta$-peptide sequence. The peptide was dissolved in water immediately before use. This small amount of protein is believed to approximate the concentration of protein observed in post-mortem samples in the brains of people who died with Alzheimer's dementia.

Treatment of the smooth muscle cells with the human protein sequence was shown to kill 70% to 85% of the smooth muscle cells apoptotically over a 1-week period as demonstrated by a bisbenzimide (Hoechst 33258) staining of the cells' nuclei. The dead cells had nuclei that were condensed and fragmented. Percentages were determined by counting normal and apoptotic nuclei in three fields with five independent measures in a fluorescence microscope. Some spatial-dependency was noticed in that cells that were judged to be normal had little amyloid accumulation as determined by thioflavin S staining and fluorescence microscopy. The earliest that a statistically significant cytotoxicity was established was at 24 hours.

The thiazolidinone (20–30 $\mu$M in 5% DMSO/water v/v) was added to the culturing media and the media was stored for 24 hours at 37° C. The thiazolidinone was shown to significantly decrease the cell death induced by the amyloid. Treatment of the cultures with vehicle alone did not alter amyloid cytotoxicity. The protective effect of CI-1004 was further established by the fact that the amyloid accumulation over the cells was reduced, thus implying that the thiazolidinone either decreased a cellular receptor for amyloid or caused the disperal of an amyloid receptor.

The foregoing biological data establish that the thiazolidinone is useful in treating and preventing acute and chronic neurodegenerative disorders. Accordingly, the compound is especially well-suited to treating and preventing stroke, head trauma, multiple sclerosis, and Alzheimer's disease.

As noted above, the thiazolidinone is additionally well-suited to treating elderly patients because of its long duration of action and its substantial lack of undesirable side effects. Toxicologic properties of the thiazolidinone were evaluated in single-dose oral and intravenous (IV) studies in mice and rats and multidose oral studies in rats and dogs. The thiazolidinone was tested in dogs and monkeys in escalating-dose oral toxicity to determine the most sensitive nonrodent species. After perivascular mononuclear infiltrates in brain were observed in the initial 13-week dog study, multidose studies were conducted in monkeys to determine if similar effects occurred in another nonrodent species. The initial 13-week dog study was repeated to evaluate the reproducibility of the perivascular effects. Dose range-finding studies were performed in pregnant rats and rabbits, and genotoxic potential was assessed in vitro and in vivo. The results of these studies establish that the toxicologic profile of the thiazolidinone is similar to that of NSAIDs, and the species studied responded in a similar qualitative and quantitative fashion. Characteristic NSAID-type hepatic enzyme induction which was not associated with overt organ toxicity was seen in rats and dogs. Nonsteroidal anti-inflammatory drug-related gastrointestinal effects in rats and dogs, and minor renal effects in rats, were observed in definitive 13-week studies. No typical NSAID-related changes were observed in monkeys treated for 13 weeks. Superficial ileo-cecal erosions identified microscopically were observed in the 13-week monkey study, but these lesions were not attributed to drug since the incidence and severity were not related to dose or systemic exposure. Based on exposure at the no-effect dose in definitive studies, the rat appears to be the most sensitive species followed by the dog and the monkey, albeit with minor differences in exposure between the species. No effects were observed in male rats given 10 mg/kg, with associated Cmax and AUC(0–24) of 0.97 μg/mL and 16.5 μg·hr/mL, respectively. Renal effects were seen in female rats at 10 mg/kg, but Cmax and AUC were approximately twice those in male rats at the same dose. These data establish that thiazolidinone is well-suited to treating a wide variety of patients, and especially elderly patients suffering from neurodegenerative disorders such as Alzheimer's disease.

The thiazolidinone can be formulated with common excipients for convenient parenteral, transdermal, and oral administration. A preferred method of treatment employs oral administration. Example 6 below illustrates the preparation of a typical capsule formulation well-suited for administering to patients to prevent neurodegenerative disorders such as stroke and head trauma, and treating patients suffering from neurodegenerative disorders such as Alzheimer's disease and multiple sclerosis.

EXAMPLE 6

| Ingredients | Quantity per 1000 Capsules | | | |
| --- | --- | --- | --- | --- |
| | 1 mg/capsule | 10 mg/capsule | 50 mg/capsule | 100 mg/capsule |
| Thiazolidinone | 1.289 g | 12.891 g | 64.455 g | 128.910 g |
| Colloidal Silicon Dioxide, NF | 2.000 g | 2.000 g | 4.000 g | 4.000 g |
| Lactose, NF | 93.000 g | 82.000 g | 51.000 g | 31.000 g |
| Corn Starch, NF | 232.711 g | 202.109 g | 121.545 g | 70.090 g |
| Croscarmellose Sodium, NF | 9.000 g | 9.000 g | 9.000 g | 9.000 g |
| Hydroxypropyl Methylcellulose, USP | 5.000 g | 5.000 g | 10.000 g | 2.000 g |
| Talc, USP | 7.000 g | 7.000 g | 10.000 g | 13.000 g |
| Purified Water, USPa | qs | qs | qs | qs |
| Total Fill Weight | 350.000 g | 320.000 g | 270.000 g | 258.000 g |

[a]Used in the manufacturing of the powder blends but is removed during drying operation. Water does not appear in the final product.

The ingredients are blended to uniformity, dried, and filled into gelatin capsules for oral administration from 1 to 4 times a day for effective prevention and treatment of neurodegenerative disorders.

What is claimed is:

1. A method for treating and preventing neurodegenerative disorders comprising administering to a patient in need of treatment an effective amount of 5-[[3,5-bis(1,1-dimethylethyl)-4-hydroxyphenyl]methylene]-2-imino-4-thiazolidinone or a pharmaceutically acceptable salt thereof.

2. A method of claim 1 wherein the compound employed is in the form of a methanesulfonate salt.

3. A method of claim 2 wherein the compound employed is (Z)-5-[[3,5-bis(1,1-dimethylethyl)-4hydroxy-phenyl]methylene]-2-imino-4-thiazolidinone methanesulfonate.

4. A method of claim 1 wherein the disorder treated is Alzheimer's disease.

5. A method of claim 1 wherein the disorder treated is multiple sclerosis.

* * * * *